US011052252B1

(12) United States Patent
Howard et al.

(10) Patent No.: US 11,052,252 B1
(45) Date of Patent: Jul. 6, 2021

(54) TRANSCRANIAL INTERVENTION TO WEAKEN AN UNDESIRABLE MEMORY

(71) Applicant: HRL Laboratories, LLC, Malibu, CA (US)

(72) Inventors: Michael D. Howard, Westlake Village, CA (US); Praveen K. Pilly, West Hills, CA (US)

(73) Assignee: HRL Laboratories, LLC, Malibu, CA (US)

(*) Notice: Subject to any disclaimer, the term of this patent is extended or adjusted under 35 U.S.C. 154(b) by 66 days.

(21) Appl. No.: 16/418,920

(22) Filed: May 21, 2019

Related U.S. Application Data

(63) Continuation-in-part of application No. 15/944,530, filed on Apr. 3, 2018, now Pat. No. 10,877,444.

(60) Provisional application No. 62/516,457, filed on Jun. 7, 2017, provisional application No. 62/752,198, filed on Oct. 29, 2018.

(51) Int. Cl.
| | | |
|---|---|---|
| *A61F 9/008* | (2006.01) | |
| *A61N 1/36* | (2006.01) | |
| *A61N 1/04* | (2006.01) | |
| *A61B 5/369* | (2021.01) | |
| *A61M 21/00* | (2006.01) | |
| *A61B 5/00* | (2006.01) | |

(52) U.S. Cl.
CPC .......... *A61N 1/36025* (2013.01); *A61B 5/369* (2021.01); *A61N 1/0484* (2013.01); *A61B 5/4836* (2013.01); *A61M 2021/0072* (2013.01); *A61N 1/0456* (2013.01)

(58) Field of Classification Search
CPC .............. A61N 1/36025; A61N 1/0484; A61N 1/0456; A61B 5/0476; A61B 5/4836; A61M 2021/0072
See application file for complete search history.

(56) References Cited

U.S. PATENT DOCUMENTS

| | | |
|---|---|---|
| 8,073,540 B2 | 12/2011 | Noren |
| 10,046,162 B1 | 8/2018 | Pilly et al. |
| 10,067,516 B2 | 9/2018 | Ramagem |

(Continued)

OTHER PUBLICATIONS

Braboszcz, C. et al., "Lost in thoughts: Neural markers of low alertness during mind wandering" NeuroImage, 54(4), pp. 3040-3047 (2011).

(Continued)

*Primary Examiner* — Michael W Kahelin
*Assistant Examiner* — George E Banis
(74) *Attorney, Agent, or Firm* — Tope-McKay & Associates

(57) ABSTRACT

Described is a system for weakening an undesirable memory. The system initiates application of a first pattern of spatiotemporally distributed transcranial stimulation via a set of electrodes to a subject who is in a calm mental state, causing association of the first pattern of spatiotemporally distributed transcranial stimulation with the calm mental state. The system then initiates application of the first pattern of spatiotemporally distributed transcranial stimulation via the set of electrodes when the undesirable memory is recalled by the subject, causing recall of the calm mental state and reconsolidation of the undesirable memory with the calm mental state.

20 Claims, 8 Drawing Sheets

(56) References Cited

U.S. PATENT DOCUMENTS

| | | | |
|---|---|---|---|
| 2014/0057232 A1* | 2/2014 | Wetmore | A61B 5/0036 |
| | | | 434/236 |
| 2014/0275838 A1 | 9/2014 | Osorio | |
| 2016/0004224 A1 | 1/2016 | Pi | |
| 2016/0063397 A1 | 3/2016 | Ylipaavalniemi | |
| 2016/0175589 A1* | 6/2016 | Wingeier | A61N 1/36025 |
| | | | 607/45 |
| 2016/0361020 A1 | 12/2016 | LeBoeuf | |
| 2017/0031449 A1* | 2/2017 | Karsten | G06Q 10/109 |
| 2017/0303842 A1 | 10/2017 | Yoshida | |
| 2018/0118219 A1 | 5/2018 | Hiei | |
| 2018/0160912 A1 | 6/2018 | Martin | |
| 2019/0239795 A1 | 8/2019 | Kotake | |

OTHER PUBLICATIONS

Trejo, L. J. et al., "EEG-Based Estimation and Classification of Mental Fatigue" Psychology, 06(05), pp. 572-589 (2015).

Healey, J. A. et al. "Detecting stress during real-world driving tasks using physiological sensors" IEEE Transactions on Intelligent Transportation Systems, 6(2), pp. 156-166 (2005).

Oweis, R. et al. "QRS Detection and Heart Rate Variability Analysis: A Survey" Biomedical Science and Engineering, 2, pp. 13-34. 10.12691/bse-2-1-3 (2014).

Rodgers, J. L. et al. "Thirteen ways to look at the correlation coefficient" The American Statistician. 42 (1): pp. 59-66 (1988).

Erden, F. et al. "Contact-free measurement of respiratory rate using infrared and vibration sensors" Infrared Physics & Technology. Nov. 1, 2015;73:pp. 88-94 (2015).

Procházka, A. "Microsoft kinect visual and depth sensors for breathing and heart rate analysis" Sensors. Jun. 28, 2016;16(7):996 (2016), pp. 1-11.

Nelder, J. et al. "Generalized Linear Models" Journal of the Royal Statistical Society. Series A (General). Blackwell Publishing. 135 (3): pp. 370-384 (1972).

Delorme, A. et al. "Eeglab: an open source toolbox for analysis of single-trial eeg dynamics including independent component analysis" Journal of neuroscience methods 134, pp. 9-21 (2004).

Daly, I. et al. "On the automated removal of artifacts related to head movement from the eeg" IEEE Transactions on neural systems and rehabilitation engineering 21, pp. 427-434 (2013).

Daly, I. et al. "What does clean eeg look like?" In Engineering in Medicine and Biology Society (EMBC), 2012 Annual International Conference of the IEEE (IEEE), pp. 3963-3966.

Herwig, U. et al. "Using the international 10-20 EEG system for positioning of transcranial magnetic stimulation" Brain topography. Dec. 1, 2003;16(2):pp. 95-99.

T. VanderPlas, J. "Understanding the Lomb-Scargle Periodogram" arXiv:1703.09824 [astro-ph.IM] (2017), pp. 1-55.

Nakagawa, S. et al. "A general and simple method for obtaining R2 from generalized linear mixed-effects models" Methods in Ecology and Evolution. Feb. 1, 2013;4(2): pp. 133-142.

Fisher, R. A. "The Use of Multiple Measurements in Taxonomic Problems" Annals of Eugenics. 7 (2): pp. 179-188 (1936).

Cortes, C. "Support-vector networks" Machine Learning. 20 (3): pp. 273-297 (1995).

Ben-Hur, A. "Support vector clustering" Journal of Machine Learning Research, 2: pp. 125-137 (2001).

Drucker, H. "Support Vector Regression Machines" Advances in Neural Information Processing Systems 9, NIPS 1996, pp. 155-161, MIT Press (1997).

Yan, X., Linear Regression Analysis: Theory and Computing, World Scientific, pp. 1-2 (2009).

Nader K, Schafe GE, Le Doux JE. Fear memories require protein synthesis in the amygdala for reconsolidation after retrieval. Nature. 2000; 406: pp. 722-726.

Foa EB. Social anxiety disorder treatments: psychosocial therapies. J. Clin. Psychiatry. 2006; 67 Suppl 12: pp. 27-30.

Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.

Bustos SG, Maldonado H, Molina VA. Midazolam disrupts fear memory reconsolidation. Neuroscience. 2006; 139: pp. 831-842.

Chan JCK, LaPaglia JA. Impairing existing declarative memory in humans by disrupting reconsolidation. Proc. Natl. Acad. Sci. 2013; 110: pp. 9309-9313.

Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008; 42: pp. 503-506.

Patel AN, Howard MD, Roach SM, Jones AP, Bryant NB, Robinson CSH, Clark VP, Pilly PK. Mental state assessment and validation using personalized physiological biometrics. Frontiers in Human Neuroscience. 2018; vol. 12, pp. 1-13.

Office Action 1 for U.S. Appl. No. 15/944,530, dated Oct. 16, 2019.
Response to Office Action 1 for U.S. Appl. No. 15/944,530, dated Jan. 16, 2020.
Office Action 2 for U.S. Appl. No. 15/944,530, dated Apr. 23, 2020.
Response to Office Action 2 for U.S. Appl. No. 15/944,530, dated Jul. 23, 2020.
Notice of Allowance for U.S. Appl. No. 15/944,530, dated Aug. 26, 2020.

* cited by examiner

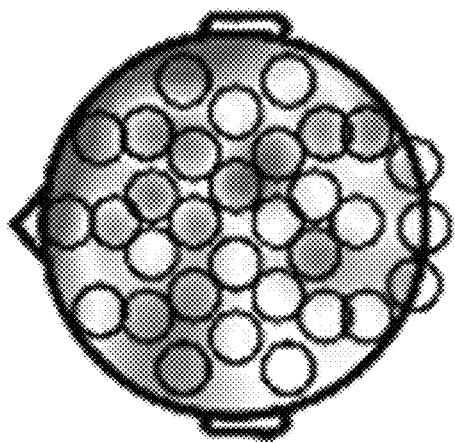
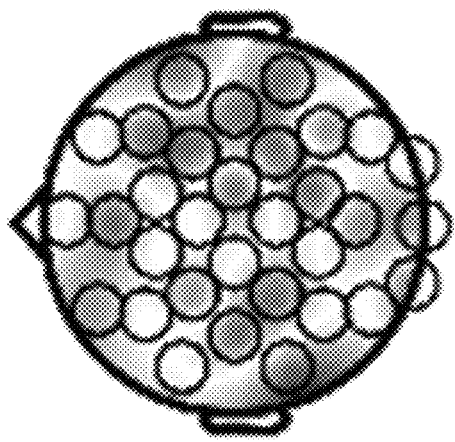
FIG. 8

TRANSCRANIAL INTERVENTION TO WEAKEN AN UNDESIRABLE MEMORY

CROSS-REFERENCE TO RELATED APPLICATIONS

The present application is a Continuation-in-Part patent application of U.S. application Ser. No. 15/944,530, filed in the United States on Apr. 3, 2018, entitled, "System and Method for Biofeedback Including Relevance Assessment," which is a Non-Provisional patent application of U.S. Provisional Application No. 62/516,457, filed in the United States on Jun. 7, 2017, entitled, "System and Method for Biofeedback Including Relevance Assessment," the entirety of which are incorporated herein by reference.

The present application is ALSO a Non-Provisional Application of U.S. Provisional Application No. 62/752,198, filed in the United States on Oct. 29, 2018, entitled, "Transcranial Intervention to Weaken Memory Reconsolidation," the entirety of which is incorporated herein by reference.

GOVERNMENT LICENSE RIGHTS

This invention was made with government support under U.S. Government Contract Number W911NF-16-C-0018 awarded by DARPA. The government has certain rights in the invention.

BACKGROUND OF INVENTION

(1) Field of Invention

The present invention relates to a system for weakening memory reconsolidation and, more particularly, to a system for weakening an undesirable memory using transcranial intervention.

(2) Description of Related Art

Traumatic memories are intense, stressful, and emotionally paralyzing. Trauma-focused cognitive behavioral therapy techniques (such as that described in Literature Reference No. 4 of the List of Incorporated Literature References) are common in psychological treatment. Behavioral therapy techniques require appointments with trained therapists for months or years of sessions. Eye movement desensitization and reprocessing (EMDR) (see Literature Reference No. 5) uses a series of eye movements and/or hand taps applied in a specific sequence in a clinical setting. Like cognitive behavioral therapy, EMDR requires appointments with trained therapists to evoke the disturbing memories and administer the treatment.

Additionally, antidepressants may be prescribed to post-traumatic stress disorder (PTSD) sufferers, but these antidepressants do not treat the causes, only the symptoms, and have the potential for psychological dependence and addiction. Other medications specifically disrupt memory reconsolidation (see Literature Reference No. 6).

As described above, prior art methods to impair existing declarative memories in humans by disrupting or modifying reconsolidation either use a behavioral re-conditioning paradigm (see Literature Reference Nos. 4 and 11) or employ drugs during or following the experience of a traumatic memory (see Literature Reference Nos. 6 and 12).

Thus, a continuing need exists for a system that employs high-definition transcranial stimulation to proactively disrupt the reconsolidation processes and weaken an undesirable memory without the use of drugs or behavioral therapy.

SUMMARY OF INVENTION

The present invention relates to a system for weakening an undesirable memory and, more particularly, to a system for weakening an undesirable memory using transcranial intervention. The system comprises one or more processors and a non-transitory computer-readable medium having executable instructions encoded thereon such that when executed, the one or more processors perform multiple operations. The system initiates application of a first pattern of spatiotemporally distributed transcranial stimulation via a set of electrodes to a subject who is in a calm mental state, thereby causing association of the first pattern of spatiotemporally distributed transcranial stimulation with the calm mental state. The system then initiates application of the first pattern of spatiotemporally distributed transcranial stimulation via the set of electrodes when the undesirable memory is recalled by the subject, thereby causing recall of the calm mental state and reconsolidation of the undesirable memory with the calm mental state.

In another aspect, the transcranial stimulation is one of weak high-definition transcranial alternating current stimulation, weak high-definition transcranial direct current stimulation, and transcranial magnetic stimulation.

In another aspect, application of the first pattern of spatiotemporally distributed transcranial stimulation is stopped following detection of a non-calm state in the subject during application of the first pattern of spatiotemporally distributed transcranial stimulation. The system then initiates application of a second pattern of spatiotemporally distributed transcranial stimulation via the set of electrodes to the subject when in the calm mental state, causing association of the second pattern of spatiotemporally distributed transcranial stimulation with the calm mental state.

In another aspect, a stress metric value is assigned based on a measured level of stress in the subject, and the system causes a perceptible change in a mobile device as an alert when the stress metric value exceeds a threshold.

In another aspect, the first pattern of spatiotemporally distributed transcranial stimulation is applied when the stress metric value is below the threshold.

In another aspect, when the stress metric value exceeds the threshold, stopping application of the first pattern of spatiotemporally distributed transcranial stimulation.

In another aspect, the present invention includes a system for initiating application of an antidote pattern of spatiotemporally distributed transcranial stimulation via a set of electrodes when the undesirable memory is recalled, thereby causing recall of a calm mental state and reconsolidation of the undesirable memory with the calm mental state.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descrip

FIG. 8 is an illustration of example stimulation patterns according to some embodiments of the present disclosure.

DETAILED DESCRIPTION

Figure 1:
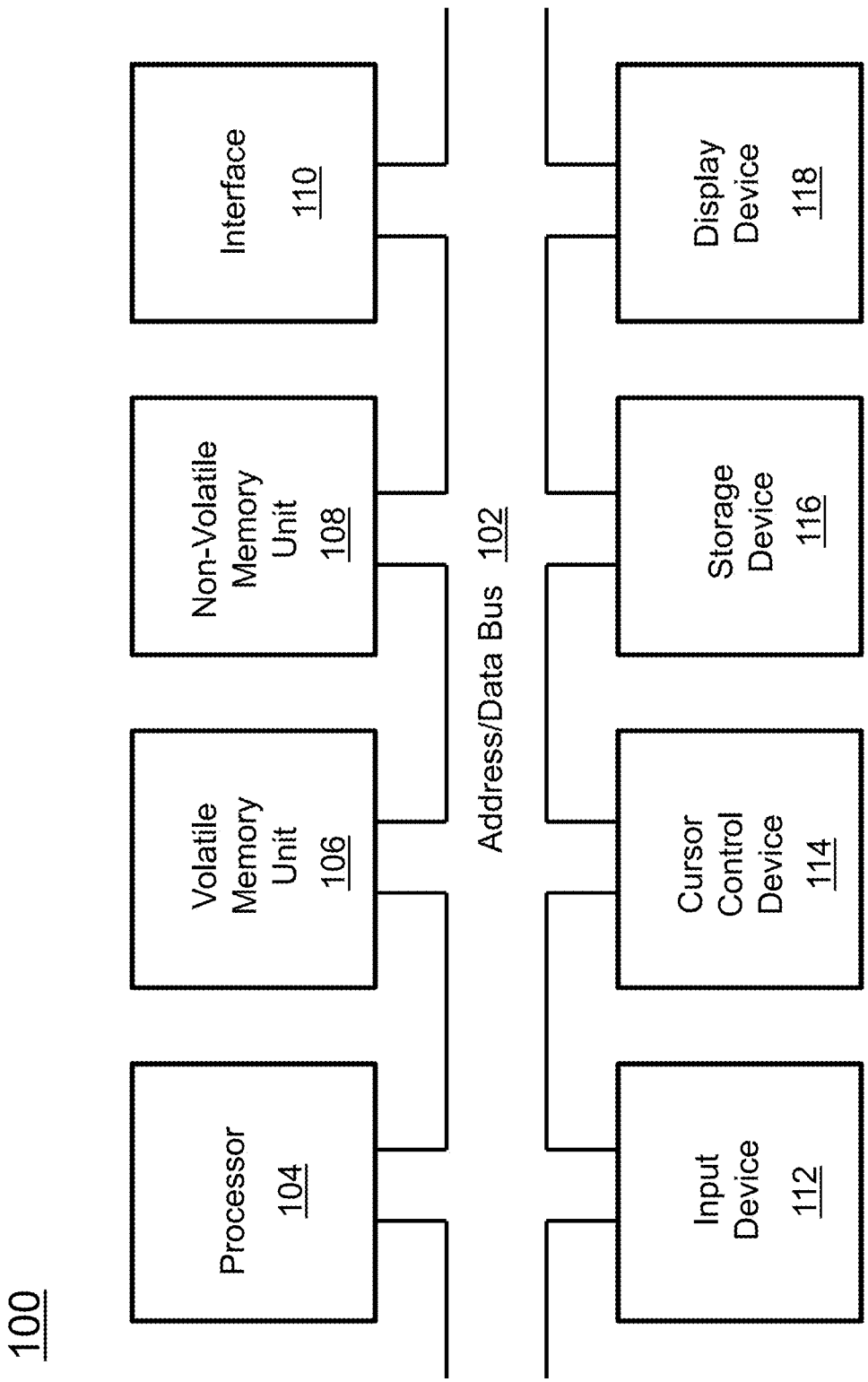
- FIG. 1 is a block diagram depicting the components of a system for weakening an undesirable memory according to some embodiments of the present disclosure.

The present invention relates to a system for weakening an undesirable memory and, more particularly, to a system for weakening an undesirable memory using transcranial intervention. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) LIST OF INCORPORATED LITERATURE AND PATENT REFERENCES

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Nader K, Schafe G E, Le Doux J E. Fear memories require protein synthesis in the amygdala for reconsolidation after retrieval. Nature. 2000; 406: 722-6.
2. Foa E B. Social anxiety disorder treatments: psychosocial therapies. J. Clin. Psychiatry. 2006; 67 Suppl 12: 27-30.
3. Seidler G H, Wagner F E. Comparing the efficacy of EMDR and trauma-focused cognitive-behavioral therapy in the treatment of PTSD: a meta-analytic study. Psychol. Med. 2006; 36: 1515-22.
4. Bustos S G, Maldonado H, Molina V A. Midazolam disrupts fear memory reconsolidation. Neuroscience. 2006; 139: 831-42.
5. Chan J C K, LaPaglia J A. Impairing existing declarative memory in humans by disrupting reconsolidation. Proc. Natl. Acad. Sci. 2013; 110: 9309-13.
6. Brunet A, Orr S P, Tremblay J, Robertson K, Nader K, Pitman R K. Effect of post-retrieval propranolol on psychophysiologic responding during subsequent script-driven traumatic imagery in post-traumatic stress disorder. J. Psychiatr. Res. 2008; 42: 503-6.
7. Patel A N, Howard M D, Roach S M, Jones A P, Bryant N B, Robinson C S H, Clark V P, Pilly P K. Mental state assessment and validation using personalized physiological biometrics. Frontiers in Human Neuroscience. 2018; vol. 12.
8. Pilly and Howard. U.S. Pat. No. 10,046,162, issued on Aug. 14, 2018, entitled "Transcranial Intervention To Weaken Traumatic Memories".

(2) PRINCIPAL ASPECTS

Various embodiments of the invention include three "principal" aspects. The first is a system for weakening an undesirable memory. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
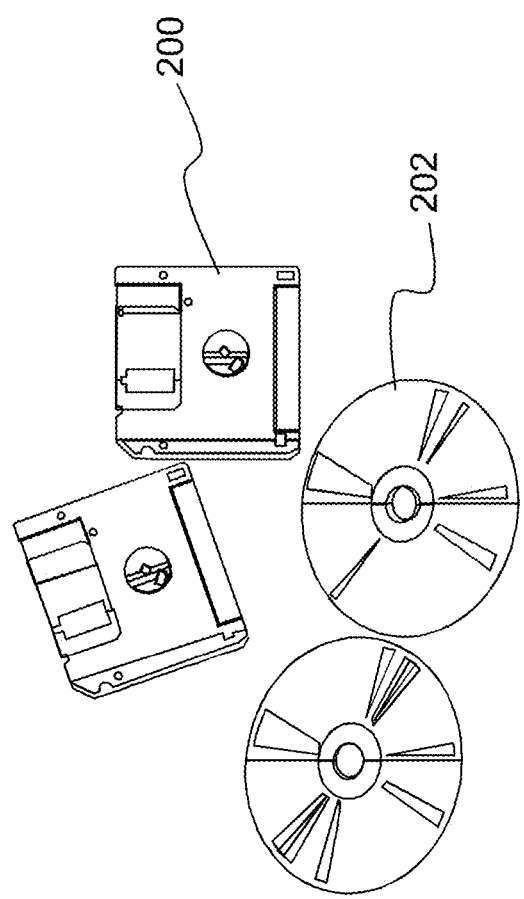
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) SPECIFIC DETAILS OF VARIOUS EMBODIMENTS

The reconsolidation hypothesis states that when a consolidated memory is recalled, it becomes unstable and susceptible to facilitation or impairment for a discrete period of time, gradually becoming reconsolidated (stabilized) again. Described herein is a system to weaken undesirable memories (e.g., post-traumatic stress) by interfering with the reconsolidation process during wake periods using targeted, transcranially applied stimulation. It is known that a memory is labile for a time after being recalled (see Literature Reference No. 1), and the invention described herein modifies the memory during this time.

Some approaches use drugs to interrupt the reconsolidation of an undesirable memory (e.g., Literature Reference No. 6). Other approaches use a behavioral paradigm to interfere with reconsolidation, and even train a related memory to alter the memory that is reconsolidated (see Literature Reference Nos. 4 and 11). The approach according to embodiments of the present disclosure, like the behavioral paradigm, alters a memory as it is being reconsolidated. However, an innovation described herein is to apply a high-definition electrical or magnetic stimulation pattern in order to cue recall of a benign memory so that it mingles with the undesirable memory during its reconsolidation. This approach is much more direct than a behavioral paradigm.

The approach is illustrated in FIGS. 4A and 4B. As depicted in FIG. 4A, upon start (element 400) of the process, a spatiotemporally distributed stimulation pattern (also referred to as the antidote pattern) is selected (element 402) for application to a calm subject (element 404). The antidote pattern is not specific to any person. Since memories are spread across the cortex of the brain, a widely distributed stimulation pattern is effective to associate with a benign feeling. It is possible that future studies could define subject-specific, localized stimulation patterns. Likewise, future studies could define subject-specific stimulation durations. As a non-limiting example of a general stimulation duration, a length of one-minute treatment can be applied any time the undesirable feelings are experienced. However, one skilled in the art might decide to apply stimulation for five minutes or some other time period, depending on the intensity of the trauma.

The system determines whether a subject is in a calm, benign state (element 406). For instance, prior art systems can determine levels of biometrics, such as heart rate variability, stress, etc. A low level of stress can be used as an indicator of a calm state. Literature Reference No. 7 discloses techniques for computing stress and two other biometrics. If the subject is in a benign state (element 406), an antidote pattern is applied to the subject (element 408), where the antidote pattern is the unique stimulation pattern designed in element 402. In other words, during a relaxed, happy (benign) state, a unique spatiotemporally distributed pattern of electrical or magnetic stimulation is applied to the scalp. Thus, the antidote pattern becomes associated with the benign state, experience, or memory (element 410). A non-limiting example of a spatiotemporally distributed pattern is a pattern over 32 electrodes limited to a total injected current limited to 2.5 milliamperes (mA) with maximum 1.5 mA current at any electrode, and 150 µA minimal current at any electrode (to avoid impedance issues). The values are based on customary values for comfort and safety. Some people are more sensitive than others to the maximum current levels, therefore, in practice, one skilled in the art would adjust maximum levels to an individual's comfort before deploying it.

The benign state can be achieved by standard relaxation techniques, such as concentrating on the breathing, mentally visiting each part of the body and telling it to relax, visualizing a happy time, etc., and these relaxation techniques may be guided or self-administered. It is necessary that the antidote pattern be applied (element 408) only while the subject is in the benign state (element 406). The test of being in a benign state (element 406) is applied, for instance, every minute that the pattern is being applied. If the test (element 406) is false, then the system returns to the subject.

FIG. 4B illustrates a method of applying the antidote pattern when a subject experiences an undesirable memory (element 412). The subject initiates application of the antidote pattern (element 414), and the antidote pattern cues recall of the benign memory (element 416) of the benign state with which the pattern was associated. The antidote pattern is used to cue recall of the benign state (both physical and mental), so it becomes intermingled with the undesirable memory. In other words, the undesirable memory becomes associated with the benign memory when it is reconsolidated (element 418).

Figure 4:
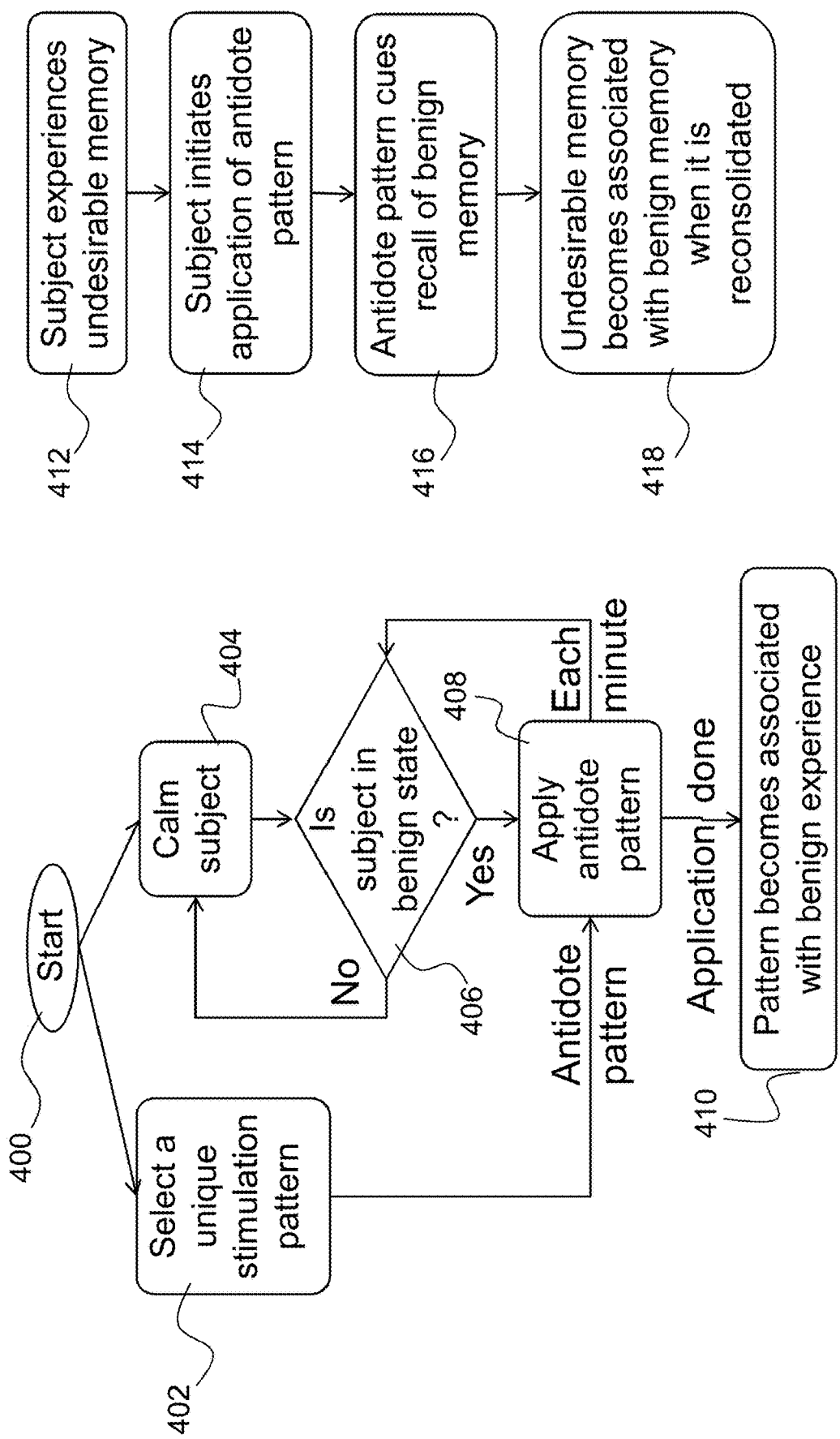
FIG. 4A is a flow diagram illustrating association of a unique stimulation pattern with a benign state according to some embodiments of the present disclosure.
FIG. 4B is a flow diagram illustrating recall of a benign state according to some embodiments of the present disclosure.
Figure 5:
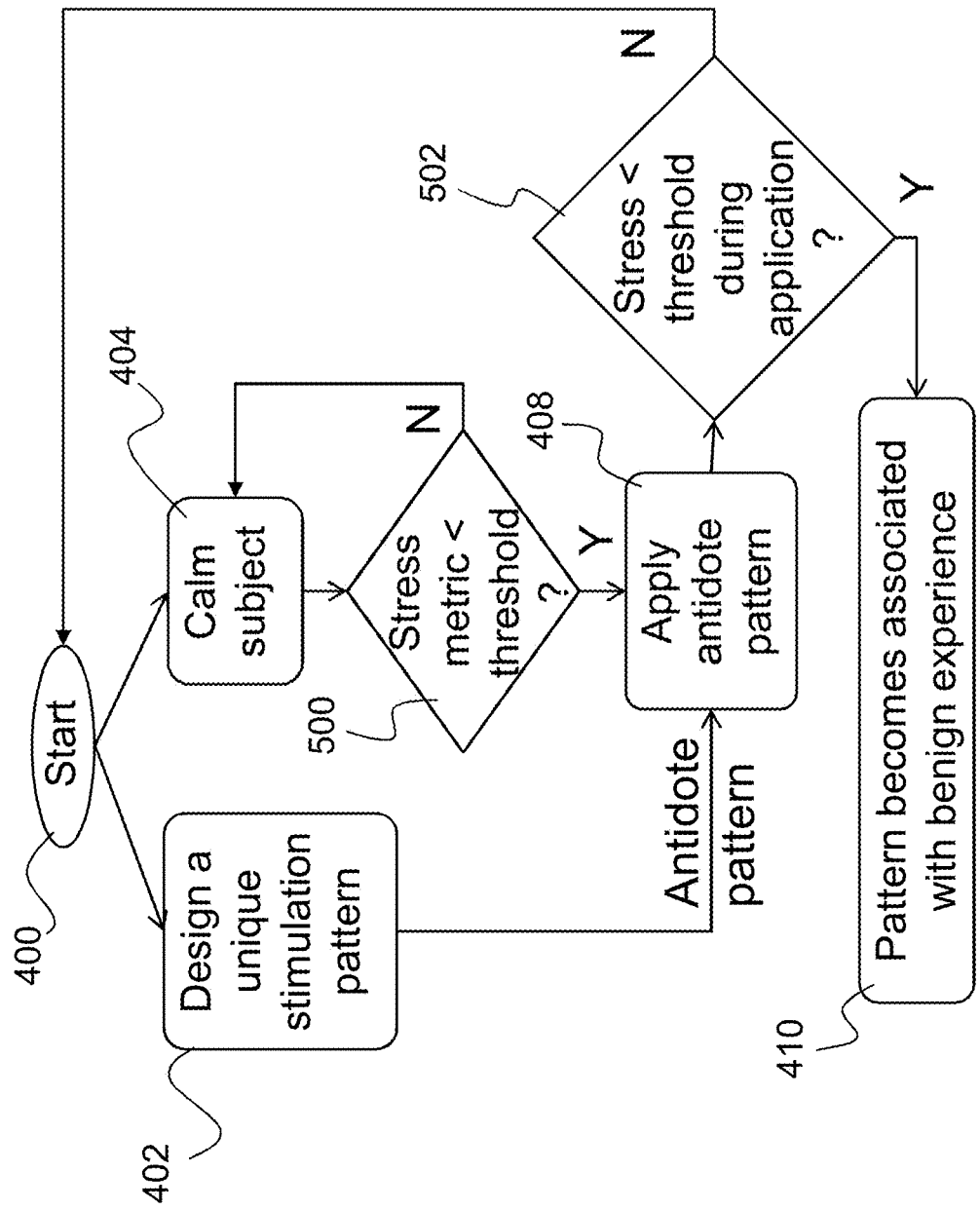
FIG. 5 is a flow diagram illustrating automated stress monitoring according to some embodiments of the present disclosure.

If the subject's benign state is interrupted while the antidote pattern is being applied, the stimulation should immediately be turned off and the process reverts to the start node (element 400) as shown in FIG. 4A, selecting a new antidote pattern. The selection is based on random distribution, constrained so that the sum over all electrodes is 2.5 mA, and no electrode supplies more than 1 mA. This is because the antidote pattern must be associated only with a benign state and reliably evoke that state when applied. Since this is critically important, and the subject may not be able to reliably report a momentary lapse of peacefulness, an automated biometrics monitoring system, such as the one shown in FIG. 5, can be used. For instance, a biofeedback system can be set up using a stress monitor (e.g., fitness watches that use heart rate variability as a measure of stress), such as those commercially available and integrated into smart watches or cell phones. A stress metric value can be connected with a perceptible change, such as a tone whose pitch is controlled by the metric (e.g., high pitch to indicate high stress, low pitch indicates low stress), or a computer screen whose brightness (e.g., bright light to indicate high stress, low light to indicate low stress) is controlled by the stress metric value. Such a biofeedback system can be used to implement the "calm subject" module (element 404) in FIG. 4. Once implemented, the "calm subject" module (element 404) can provide (i.e., display, play audio) instructions to the user. For example, a well-known method to reduce stress is to focus on breathing slowly, counting each breath up to ten, and then restarting at one. Additional instructions can include instructing the user to do this for five minutes while sitting calmly with eyes closed, or while showing relaxing nature scenes on a monitor. Another method is a guided relaxation, instructing the subject to relax each part of the body from toes to head, and consciously relax each part. These methods are widely available online.

A threshold for the stress metric value can be established by having the subject use the stress monitoring device during a day or two, finding the maximum and minimum stress over the period. The minimum stress metric may be further reduced by having the subject perform the relaxation exercises described above with biofeedback to determine the lowest stress level attainable by the subject at this time. Using those values for maximum and minimum stress, a reasonable threshold to set in the test in FIG. 5 might be 10% higher than the minimum stress level. The system compares the stress metric value to the threshold (element 500). If the stress metric value is less than the threshold, then the antidote pattern can be applied (element 408). Alternatively, if the stress metric value is greater than the threshold, the subject can perform the relaxation exercises to calm the subject (element 404) following instructions to go through a set of guided relaxation exercises. During application of the antidote pattern (element 408), if the stress metric value is less than the threshold, then the antidote pattern becomes associated with the benign experience (element 410). However, if the stress metric value is greater than the threshold during application of the antidote pattern, then the stimulation is turned off automatically and the process goes back to the start node (element 400).

Additionally, to get a good association between the antidote pattern and the benign state, it is only necessary to stimulate the subject for a short period of time in any one trial. A short period would be in the range of 5 minutes. For maximum association, a number of trials can be used, where each trial is preceded by a biofeedback relaxation session. The same antidote pattern would be used in each of these trials. The proviso is that if the subject's stress level rises above threshold during application of the antidote pattern in any trial, that antidote pattern must be rejected and the entire process must begin again. Since probability of this rises with every trial as the subject tires, the number of trials should be limited. Thus, there is a balance between the advantage of extra trials to strengthen the association of the antidote pattern with a series of benign states versus the disadvantage of possibly tiring and frustrating the subject and having to start over. As a non-limiting example, five trials of five minutes each (with a break between them) would be a reasonable compromise, depending on the subject.

The "antidote pattern" is a unique pattern of weak high-definition transcranial alternating or direct current stimulation (HD-tACS or HD-tDCS) or transcranial magnetic stimulation (TMS). "High-definition" means administered by a large number of electrodes (typically 32 to 64) distributed across the scalp. "Weak" current stimulation means that the total current across all electrodes is less than around 2.5 milliamperes (mA), and no single electrode transmits more than 1 mA. One embodiment employs tDCS, but equivalent stimulation patterns can be created using tACS or TMS. Herein, tCS refers to any of the aforementioned transcranial stimulation methods. Indeed, any method that can create a reproducible pattern of cell excitability across distributed brain areas can be used to produce the antidote pattern.

The antidote pattern is applied when the subject is in a benign state, and this causes the antidote pattern to become associated with the benign memory (FIG. 4A); it will feel like no more than a minor tingling sensation. It is then possible to use the antidote pattern at a later time as a cue to recall the benign state. When a subject relives a traumatic episode or other undesirable memory, that memory is labile for a short period (possibly up to hours, depending on the memory), and susceptible to modification. However, the antidote pattern will be most efficacious if applied right after the undesirable memory is recalled (FIG. 4B). The patient can apply the antidote pattern when the undesirable memory is recalled, or this system can be used in clinical settings, where the negative memory is evoked in the patient by a therapist and then the antidote pattern applied. Each episode with stimulation-based treatment will weaken the memory further.

It is possible that a single antidote pattern would be enough to weaken the one or more undesirable memories a particular patient may want to weaken. This pattern only needs to be unique; therefore, it may be constructed by choosing random values within the maximum amplitude range to stimulate each location on the scalp. An alternative implementation would be to create a number of antidote patterns, designing them to be as different as possible from each other. Euclidean distance is a metric that can be used to assess amount of orthogonality between patterns. For example, maximum orthogonality for a pattern of stimulation to N locations on the scalp would be to give maximum amplitude to N/2 locations subject to the previously mentioned overall limit and the aforementioned minimum amplitude to the other N/2 locations. Each of the multiple antidote patterns should be associated with a different benign episode (i.e., each pattern is applied in a different session when the subject is relaxed). This would provide a number of antidote patterns, any of which could be applied (randomly chosen) whenever the undesirable memory is recalled.

Note that after associating the antidote pattern with a benign state, if it is subsequently used to interrupt reconsolidation of a traumatic memory, it will become associated with the traumatic memory to some extent. If the number of traumatic episodes in which a particular antidote pattern is used exceeds the number of trials used to associate the antidote pattern with a benign state, then the antidote pattern will become tainted by the trauma and a new pattern must be created. In fact, since the traumatic memory is emotionally charged (and the benign state is not), it will reduce the effectiveness of the antidote pattern every time it is used to weaken the traumatic memory. Therefore, particularly at the start of therapy using this method, the antidote pattern should be discarded after use to weaken one or two traumatic episodes, and another antidote pattern should be trained, as shown in FIG. 4A, and used the next time a traumatic episode is experienced.

It should be noted that it is not necessary for the antidote pattern stimulation to be perfectly transmitted deep into the brain. Some amount will be shunted by the skull anyway. It is also not necessary for the antidote pattern, once associated with a benign state, to perfectly cue recall of the benign state. It is sufficient that some aspects of the benign state will be associated with whatever amount of stimulation from the antidote pattern gets through to the cortex, because when the undesirable memory is recalled and the antidote pattern is applied, this will modify the reconsolidation of the memory.

Figure 6:
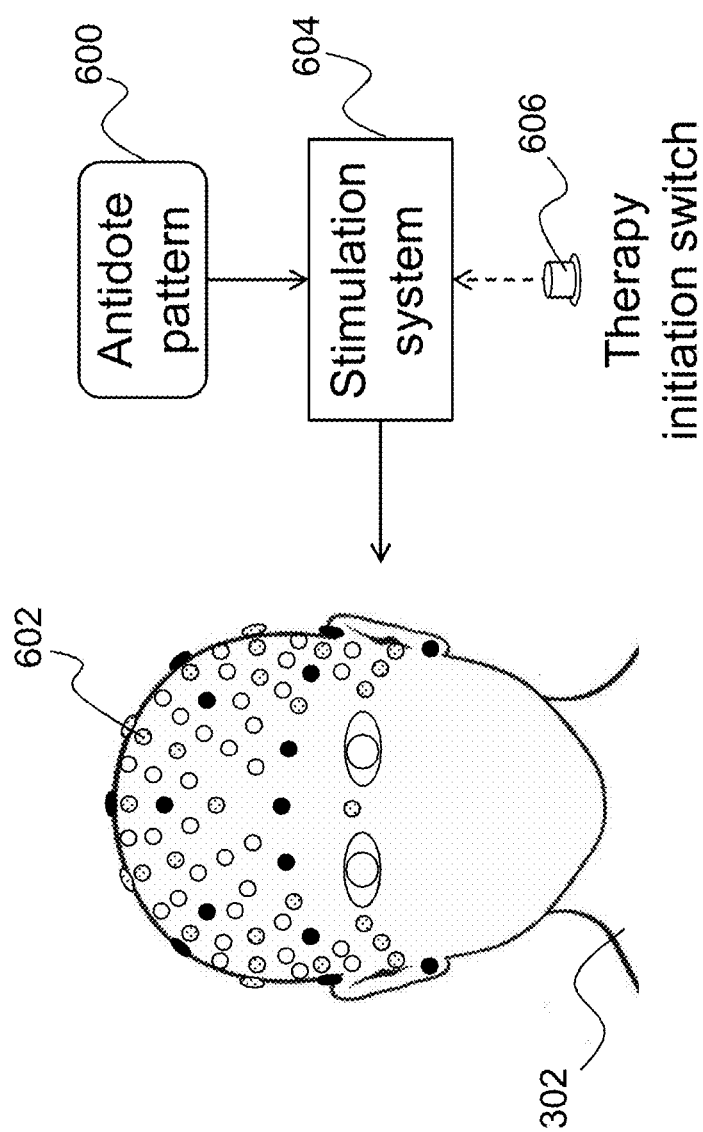
FIG. 6 is an illustration of the architecture of the system according to some embodiments of the present disclosure.
Figure 7:
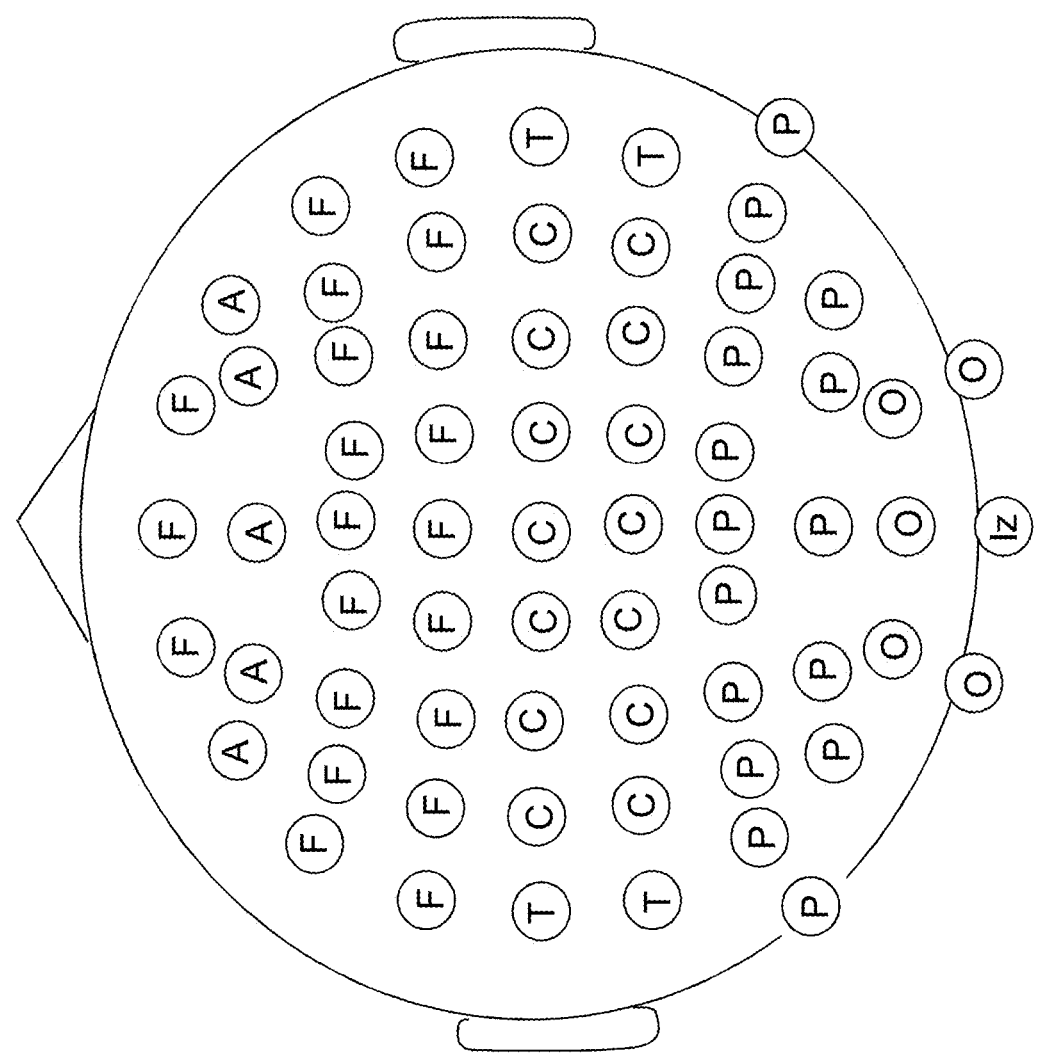
FIG. 7 is an illustration of a layout of electrodes according to some embodiments of the present disclosure.

FIG. 6 illustrates the architecture of the invention according to embodiments of the present disclosure. In the depicted implementation, tCS is used to administer the antidote pattern (element 600). The subject (element 302) wears a high-density array of electrical stimulators (element 602) on the head, such as HD-tCS (high-definition tCS). The antidote pattern (element 600) is the unique stimulation pattern (element 402) of FIGS. 4A and 5. The antidote pattern (element 600) of stimulation is applied at each location of the scalp. An example of locations of electrode positioning is the standard "10-20" pattern of electrode locations known to those skilled in the art. An illustration of a layout of electrode locations is shown in FIG. 7, where circles represent electrodes positioned on the scalp/head. In FIG. 7, "F" represents frontal, "T" represents temporal, "P" represents parietal, "O" represents occipital, and "C" represents central, all of which refer to lobes or regions of the brain. FIG. 8 depicts examples of two possible stimulation patterns, where varying shading represents varying intensities of current. For instance, no shading represents no stimulation at those brain regions, light shading represents 0.75 mA of stimulation at those brain regions, and dark shading represents 1.5 mA of stimulation at those brain regions.

Figure 3:
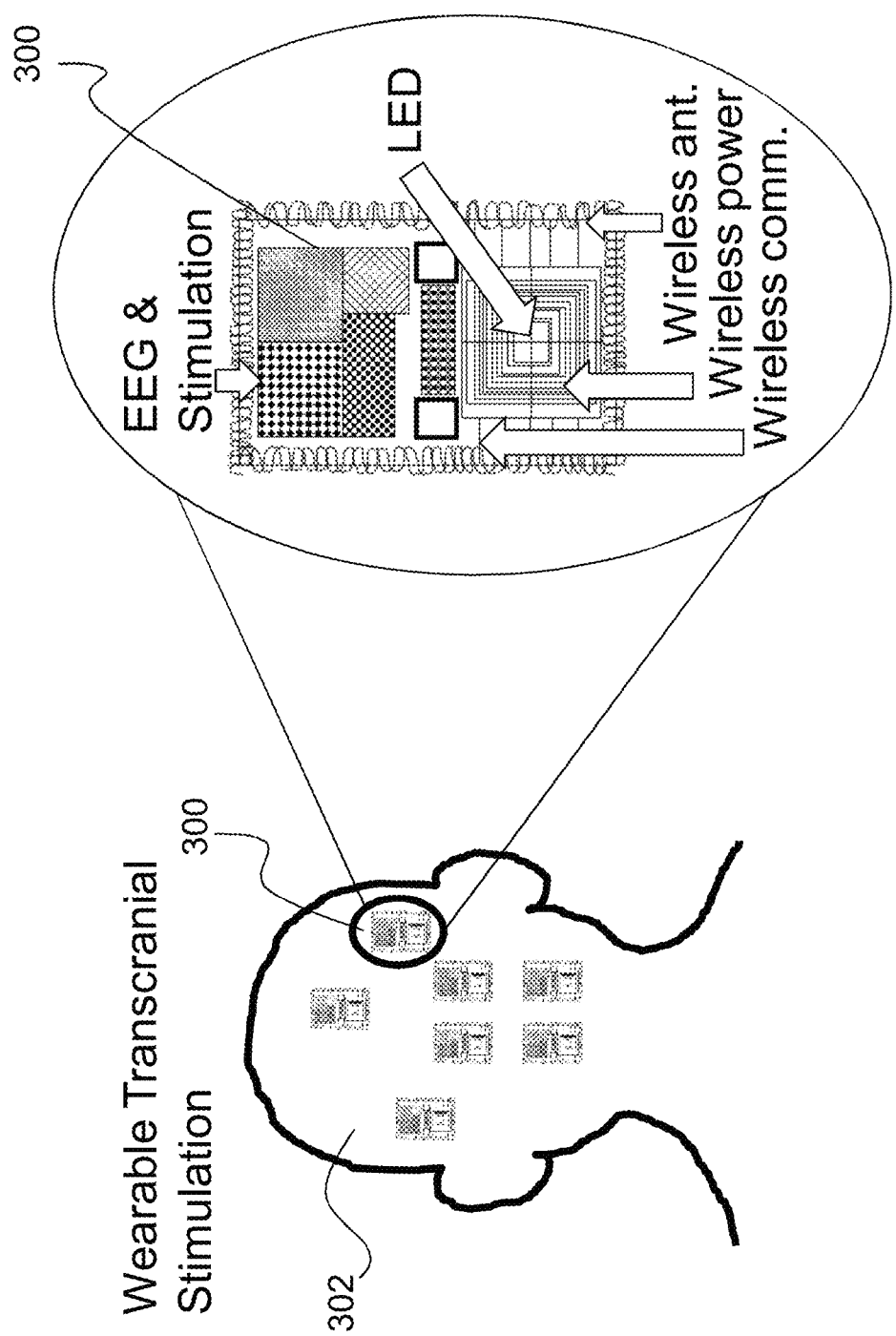
FIG. 3 is an illustration of wearable transcranial stimulation according to some embodiments of the present disclosure.

In one embodiment, the stimulation system 604 is a commercial product that can be purchased from such manufacturers as Neuroelectrics (located at 210 Broadway, Suite 201, Cambridge 02139, Massachusetts) for HD-tCS, which can also supply electrodes. In one embodiment, a therapy initiation switch (element 606) is configured to actuate control of the stimulation system 604. The therapy initiation switch (element 606) can be utilized by the user or another person (e.g., doctor, therapist) to initiate. As illustrated in FIG. 3, this stimulator array can be engineered in a more ergonomic design, such as an electronic sensor 300 that attaches to the scalp of the subject 302. Of course, if TMS is used, the head is surrounded by a magnet rather than the electrodes shown.

The approach described herein will allow, for the first time, a targeted personalized closed-loop system for weakening the specific memories that are bothering the patient. A commercial company MC-10 (located at 10 Maguire Road Building 3, 1st Floor, Lexington, Mass. 02421) develops virtually invisible, conformal, and stretchable electronic sensors 300 that adhere to the skin. In one embodiment of the invention, stimulation electrodes can be added to stretchable EEG sensors 300, as illustrated in FIG. 3.

Traumatic memories are intense, stressful, and emotionally paralyzing. The targeted transcranial neurostimulation system according to embodiments of the present disclosure will treat people of post-traumatic stress without resorting to pharmaceuticals. The first stage of transition would be a clinical system, for lab use where the disturbing memory needs to be artificially evoked. A second stage would be a home system that can be either self-initiated or works automatically. A final stage would be a portable personal therapy system that also can be operated by a naïve user with minimal supervision.

The system described herein has goals similar to trauma-focused cognitive behavioral therapy techniques (e.g., Literature Reference No. 4) common in psychological treatment. However, unlike such techniques that require appointments with trained therapists for months or years of sessions, the present invention can be applied any time, throughout the day, by the patient. The patient is treated as he/she goes about their normal routine (not in a clinical session), so therapy can be applied when something triggers the feelings. The patient can get treatment as simply as pushing a button, not making an appointment for some future time.

In addition, unlike current approaches, the therapeutic procedure provided by the present invention does not require drugs. The system can be self-activated when the subject experiences traumatic memories. The therapy can be self-applied, and does not require supervision by a doctor or a psychological therapist. The therapy is targeted; it is applied only during the reconsolidation period of the undesirable memory (on the order of minutes) compared with a drug treatment with effects that can last for many hours and have unintended systemic chemical side-effects. Finally, there is no need for the subject to attend frequent behavioral therapy sessions.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for weakening an undesirable memory during wake periods, the system comprising:
one or more processors and a non-transitory memory having instructions encoded thereon such that when the instructions are executed, the one or more processors perform operations of:
during a wake period of a subject, initiating application of a first pattern of spatiotemporally distributed transcranial stimulation via a set of electrodes to the subject who is in a calm mental state, thereby causing association of the first pattern of spatiotemporally distributed transcranial stimulation with the calm mental state; and
initiating application of the first pattern of spatiotemporally distributed transcranial stimulation via the set of electrodes when the undesirable memory is recalled by the subject, thereby causing recall of the calm mental state and reconsolidation of the undesirable memory with the calm mental state.

2. The system as set forth in claim 1, wherein the transcranial stimulation is one of weak high-definition transcranial alternating current stimulation, weak high-definition transcranial direct current stimulation, and transcranial magnetic stimulation.

3. The system as set forth in claim 1, wherein the one or more processors further perform operations of:
stopping the application of the first pattern of spatiotemporally distributed transcranial stimulation following detection of a non-calm state in the subject during application of the first pattern of spatiotemporally distributed transcranial stimulation; and
initiating application of a second pattern of spatiotemporally distributed transcranial stimulation via the set of electrodes to the subject when in the calm mental state, causing association of the second pattern of spatiotemporally distributed transcranial stimulation with the calm mental state.

4. The system as set forth in claim 1, wherein the one or more processors further perform operations of:
assigning a stress metric value based on a measured level of stress in the subject; and
causing a perceptible change in a mobile device as an alert when the stress metric value exceeds a threshold.

5. The system as set forth in claim 4, wherein the first pattern of spatiotemporally distributed transcranial stimulation is applied when the stress metric value is below the threshold.

6. The system as set forth in claim 4, wherein when the stress metric value exceeds the threshold, stopping application of the first pattern of spatiotemporally distributed transcranial stimulation.

7. A computer implemented method for weakening an undesirable memory during wake periods, the method comprising acts of:
causing one or more processors to execute instructions encoded on a non-transitory computer-readable medium, such that upon execution, the one or more processors perform operations of:

during a wake period of a subject, initiating application of a first pattern of spatiotemporally distributed transcranial stimulation via a set of electrodes to the subject who is in a calm mental state, thereby causing association of the first pattern of spatiotemporally distributed transcranial stimulation with the calm mental state; and initiating application of the first pattern of spatiotemporally distributed transcranial stimulation via the set of electrodes when the undesirable memory is recalled by the subject, thereby causing recall of the calm mental state and reconsolidation of the undesirable memory with the calm mental state.

8. The method as set forth in claim 7, wherein the transcranial stimulation is one of weak high-definition transcranial alternating current stimulation, weak high-definition transcranial direct current stimulation, and transcranial magnetic stimulation.

9. The method as set forth in claim 7, wherein the one or more processors further perform operations of:

stopping the application of the first pattern of spatiotemporally distributed transcranial stimulation following detection of a non-calm state in the subject during application of the first pattern of spatiotemporally distributed transcranial stimulation; and initiating application of a second pattern of spatiotemporally distributed transcranial stimulation via the set of electrodes to the subject when in the calm mental state, causing association of the second pattern of spatiotemporally distributed transcranial stimulation with the calm mental state.

10. The method as set forth in claim 7, wherein the one or more processors further perform operations of:

assigning a stress metric value based on a measured level of stress in the subject; and causing a perceptible change in a mobile device as an alert when the stress metric value exceeds a threshold.

11. The method as set forth in claim 10, wherein the first pattern of spatiotemporally distributed transcranial stimulation is applied when the stress metric value is below the threshold.

12. The method as set forth in claim 10, wherein when the stress metric value exceeds the threshold, stopping application of the first pattern of spatiotemporally distributed transcranial stimulation.

13. A computer program product for weakening an undesirable memory during wake periods, the computer program product comprising:

computer-readable instructions stored on a non-transitory computer-readable medium that are executable by a computer having one or more processors for causing the processor to perform operations of:

during a wake period of a subject, initiating application of a first pattern of spatiotemporally distributed transcranial stimulation via a set of electrodes to the subject who is in a calm mental state, thereby causing association of the first pattern of spatiotemporally distributed transcranial stimulation with the calm mental state; and initiating application of the first pattern of spatiotemporally distributed transcranial stimulation via the set of electrodes when the undesirable memory is recalled by the subject, thereby causing recall of the calm mental state and reconsolidation of the undesirable memory with the calm mental state.

14. The computer program product as set forth in claim 13, wherein the transcranial stimulation is one of weak high-definition transcranial alternating current stimulation, weak high-definition transcranial direct current stimulation, and transcranial magnetic stimulation.

15. The computer program product as set forth in claim 13, wherein the one or more processors further perform operations of:

stopping the application of the first pattern of spatiotemporally distributed transcranial stimulation following detection of a non-calm state in the subject during application of the first pattern of spatiotemporally distributed transcranial stimulation; and initiating application of a second pattern of spatiotemporally distributed transcranial stimulation via the set of electrodes to the subject when in the calm mental state, causing association of the second pattern of spatiotemporally distributed transcranial stimulation with the calm mental state.

16. The computer program product as set forth in claim 13, wherein the one or more processors further perform operations of:

assigning a stress metric value based on a measured level of stress in the subject; and causing a perceptible change in a mobile device as an alert when the stress metric value exceeds a threshold.

17. The computer program product as set forth in claim 16, wherein the first pattern of spatiotemporally distributed transcranial stimulation is applied when the stress metric value is below the threshold.

18. The computer program product as set forth in claim 16, wherein when the stress metric value exceeds the threshold, stopping application of the first pattern of spatiotemporally distributed transcranial stimulation.

19. A system for weakening an undesirable memory during wake periods, the system comprising:

one or more processors and a non-transitory memory having instructions encoded thereon such that when the instructions are executed, the one or more processors perform operations of:

during a wake period of a subject, initiating application of an antidote pattern of spatiotemporally distributed transcranial stimulation via a set of electrodes when the undesirable memory is recalled, thereby causing recall of a calm mental state and reconsolidation of the undesirable memory with the calm mental state.

20. A computer implemented method for weakening an undesirable memory during wake periods, the method comprising acts of:

causing one or more processors to execute instructions encoded on a non-transitory computer-readable medium, such that upon execution, the one or more processors perform operations of:

during a wake period of a subject, initiating application of an antidote pattern of spatiotemporally distributed transcranial stimulation via a set of electrodes when the undesirable memory is recalled, thereby causing recall of the calm mental state and reconsolidation of the undesirable memory with the calm mental state.

\* \* \* \* \*